United States Patent [19]

North, Jr.

[11] Patent Number: 4,506,018
[45] Date of Patent: Mar. 19, 1985

[54] BLOOD DILUENT
[75] Inventor: Howard L. North, Jr., Newfoundland, N.J.
[73] Assignee: Becton, Dickinson and Company, Paramus, N.J.
[21] Appl. No.: 454,793
[22] Filed: Dec. 30, 1982
[51] Int. Cl.³ .............................................. G01N 33/16
[52] U.S. Cl. ........................................ 436/10; 436/15; 252/408.1
[58] Field of Search ................... 436/10, 15, 17, 18; 23/230 B; 252/408

[56] References Cited

U.S. PATENT DOCUMENTS

| | | | |
|---|---|---|---|
| 2,674,619 | 4/1954 | Lundsted | 252/353 |
| 3,450,502 | 6/1969 | Hymes | 23/258.5 |
| 3,577,522 | 5/1971 | Hymes | 424/78 |
| 3,590,125 | 6/1971 | Hymes | 424/78 |
| 3,850,903 | 11/1974 | Garcia et al. | 260/112 B |
| 3,915,643 | 10/1975 | Gindler | 23/230 B |
| 3,962,125 | 6/1976 | Armstrong | 252/408 |
| 4,102,810 | 7/1978 | Armstrong | 252/408 R |
| 4,184,848 | 1/1980 | Batz et al. | 23/230 B |
| 4,229,726 | 11/1981 | Crews et al. | 252/408 |
| 4,322,313 | 3/1982 | Raaijmakers | 252/408 |
| 4,389,490 | 6/1983 | Crews et al. | 436/10 |

OTHER PUBLICATIONS

"Inhibitory Effect of Non-Ionic Detergents on Osmotic Lysis of Human Red Blood Cells", *European J. Physiology*, vol. 343, Suppl. R1 1973.
"Desaggregation of Human Red Blood Cells . . .", Acta haemat. 53: 82–89, (1975), Gaehtgens et al., Univ. of Koln, Koln.
"Combined and Individual Protection by Pluronic Polyols . . .", *Cryobiology*, 11, 285–295, (1974), Voss et al.

*Primary Examiner*—Ben R. Padgett
*Assistant Examiner*—T. J. Wallen
*Attorney, Agent, or Firm*—R. P. Grindle

[57] ABSTRACT

An improved multi-purpose blood diluent is provided which is isotonic, with a neutral pH for avoiding cell volume change. The diluent of the invention provides balance between the effects on cell volume of a preservative for the solution, and the effects of a surfactant. The diluent of the invention is particularly useful as a carrier for blood samples in instruments which automatically provide medical diagnostic determinations of blood samples. The diluent herein includes conventional sodium and potassium chlorides as electrolytes, pH buffers, such as monobasic and dibasic phosphate, and ethylene diamine tetraacetic acid to control and chelate the divalent cations. The balanced preservative-surfactant combination may include, for example, 2-phenoxyethanol with certain ethylene oxide-polypropylene glycol condensation products.

7 Claims, 1 Drawing Figure

BLOOD DILUENT

BACKGROUND AND STATEMENT OF THE INVENTION

This invention relates generally to blood diluents for blood cell counting and sizing. More particularly, this invention relates to an improved multi-purpose blood diluent for use in the hematological enumeration of blood cells and the determination of hemoglobin concentration, wherein electronic particle analysis using various scanning devices is obtained. Because of this, the solution must be a stable water solution including chemical salts to provide an electrolytic solution together with other components to obtain certain desirable characteristics.

Routinely, a medical diagnostic procedure includes analyzing and testing blood samples of a patient in order to make certain classic determinations relative to the blood sample. Instrumentation which will accept a patient's blood sample and process the sample automatically and continuously is described in U.S. Pat. Nos. 4,282,902; 4,165,484; 4,240,029 and 4,110,604. The multi-purpose blood diluent described and claimed in this application is suitable for use in such instrumentation as described in these patents, as well as other electronic particle counting instrumentation for analyzing the components of a blood sample.

Thus, in the use of such instrumentation, it is necessary that accurate and successful dilution of a blood sample is made prior to the analysis. The diluent must include proper electrolyte components so as to operate in the system. By the same token, the diluent must also be appropriate for handling the blood cells so as not to effect any change in the blood cells prior to the analysis thereof. For this reason, the blood diluent must be isotonic and osmotically balanced relative to the solutions in the blood cells. The resistance of the blood cells, for example, to lysing for purposes of hemoglobin determinations must not be altered sufficiently to interfere with satisfactory lysing of red blood cells. The solution must have a neutral pH in order to avoid cell swelling or shrinking. It is well known that red blood cell volume is directly related linearly to the reciprocal of the osmolality of the medium in which they are suspended for a period of time up to a few hours. Thus, when such cells are placed in an isotonic medium matching the osmolality of the plasma, they remain unchanged. Placed in an hypotonic medium, water enters the cell membranes and the cells swell. Placed in a hypertonic medium, on the other hand, the cells shrink, because water is drawn out. In extreme cases, swelling is to such a degree that lysis takes place, or shrinking is such that there is very little water in the cells.

All such suspension mediums or diluents contain preservatives, as will be understood, but the preservatives must not alter cell membrane permeability or produce either swelling or shrinking or any negligible change. Surfactants, which are common ingredients in such diluents can also produce similar changes in the cell membrane. It is important, therefore, to select a proper preservative and surfactant component in the diluent, and to select their concentrations so that the swelling of one can offset the shrinking tendency of the other, for example. Alternatively, the tonicity of the diluent may be adjusted to offset cell volume change tendencies produced by a preservative. The net desired effect is neither swelling nor shrinking.

With this invention, such a diluent with the desired balance of properties is provided. The diluent includes, also, sodium and potassium chlorides as electrolytes, and pH buffers, such as monobasic and dibasic phosphates. Ethylene diamine tetraacetic acid is included in the diluent solution to control and chelate divalent cations.

If blood cells are suspended in an isotonic diluent containing a preservative, the cells will generally swell or shrink. The direction of swelling or shrinking may depend upon the preservative used which may be, for example, bacteriocidal, bacteriostatic, fungicidal or fungistatic. While the bacteriocidal preservatives kill bacteria they do not necessarily kill bacterial spores. The bacteriostats on the other hand, inhibit growth of bacteria and bacteriocidal spores. The weaker static action of a bacteriostat is preferred, in accordance herewith, because it is sufficient and may often be obtained by a lower concentration of the preservative. At any rate, it is a significant factor of the invention, as described herein, that the effects of the preservative component of the diluent solution in effecting any change in the blood cells is balanced by the surfactant component. The surfactant component of an isotonic diluent may also effect blood cells to cause cell shrinking or swelling. Some surfactants, for example, may cause lysis of the red blood cells, and a few might even dissolve the red blood cell membranes.

From the foregoing, it is clear that a preservative which changes the red blood cell volume in one direction, and a surfactant which changes the red blood cell volume in the opposite direction can be used together to produce a neutral effect on the cell volume and it is to this particular arrangement in a blood diluent that this invention is particularly directed. Such a combination of preservative-surfactant may include, in accordance with this invention, a variety of preservatives such as, for example, sodium hypochlorite, phenethyl alcohol, benzyl alcohol, etc. The preferred preservative is 2 phenoxyethanol which may be combined with a polyoxyethylene-polyoxypropolyene glycol non-ionic surfactant containing, preferably at least 80% ethylene oxide. Generally, the surfactant may be, for example, ethylene oxide polypropylene glycol condensation products. Such products are available in the market, and one source of such products are designated "Pluronics", products of BASF Wyandotte Corporation, Wyandotte, Mich. 48192. Other products of BASF Wyandotte which may be used are non-ionic surfactants which are structurally tetrafunctional block copolymers consisting of a backbone of ethylenediamine, to which are attached, at four locations, variable links of propylene oxide to which are attached variable links of ethylene oxide. These are entitled "Tetronic" products of BASF.

In considering generally the conditions for preparing the blood diluent solution, in accordance herewith, it may be well to note that satisfactory results have been achieved by a solution containing within the range of between about 6 and 12 grams per liter of sodium chloride as an electrolyte, and preferably 8.795 grams per liter; within the range of between about 0 and 1 grams per liter of potassium chloride as an electrolyte, and preferably 0.28 grams per liter; within the range of between about 0 and 1 grams per liter of potassium dihydrogen phosphate as a pH buffer, and preferably 0.26 grams per liter; within the range of between about 0 and 5 grams per liter disodium hydrogen phosphate as a second pH buffer, and preferably 2.35 grams per liter; within the range of between about 0 and 1 grams per liter disodium ethylenediamine tetraacetic acid, and preferably 0.36 grams per liter; within the range of between about 0.5 and 10 milliliters per liter of a preservative and preferably 2.0 milliliters per liter of a preservative; and within the range of between about 0.001 and 10 grams per liter of a surfactant and preferably 0.5 grams per liter. In this connection, it will be understood that it is one of the features of this invention to control the surfactant, and preservative content of the solution within the ranges noted, so that the effects of one on the mean corpuscular volume (MCV) of the red blood cells (RBC) added will be offset by the effects of the other.

As discussed above, it is important to select the preservative which will provide the desired preservation of the solution and which will inhibit growth of bacteria and bacterial spores without undue action on the blood cells present in the sample under consideration. Any reaction of the preservative, in accordance herewith, on the sample is to be balanced by the nature of the surfactant present. In the selection of the preservative, it is important that the effect on the sample be "mild" in its action. This avoids the need for exceptional accuracy in matching the concentrations of either the preservative or the surfactant reagent or their time courses of action. That is, the use of a slow-acting preservative and a fast-acting surfactant (or vice versa) may result in a neutral condition of no net volume change at final steady-state conditions. However, during the transient condition in order to obtain the stable condition, a mismatch in effects may prevail and cell volumes may change, resulting in erroneous assays. Thus, in the ideal case, neither the preservative nor the surfactant will change cell volumes at all by themselves. Such an ideal is not present, and it is important, therefore, to select the balance between the two so that their concentrations optimize the desirable properties of each.

Thus, the preferred preservative in accordance with the blood diluent of this invention is 2-phenoxyethanol, present in a concentration of 2.0 milliliters per liter. The 2-phenoxyethanol is relatively mild in its reaction to blood cells in a sample under investigation. Moreover, it effectively balances against the results of the surfactant selected in accordance with this invention. One useful surfactant in this invention is PLURONIC F68 which is a non-ionic surfactant of polyoxyethylene-polyoxypropylene glycol containing 80% ethylene oxide. PLURONIC F108 is especially preferred and contains ethylene oxide also in the amount of 80%. It is present in the diluent in a concentration within the range of between about 0.001 and 10 grams per liter, and preferably 0.5 grams per liter. Other PLURONIC as well as TETRONIC surfactants may also be used which vary in their ethylene oxide content. These compounds are described in detail in U.S. Pat. No. 2,674,619 which patent is hereby incorporated by reference in its entirety. That patent describes the preparation of the polyoxyethylene-polyoxypropylene compounds useful as the surfactants in this invention.

With the foregoing and additional objects in view, this invention will now be described in more detail, and other objects and advantages thereof will become apparent from the following description, the accompanying drawing, and the appended claims.

DETAILED DESCRIPTION OF THE DRAWING

Figure 1:
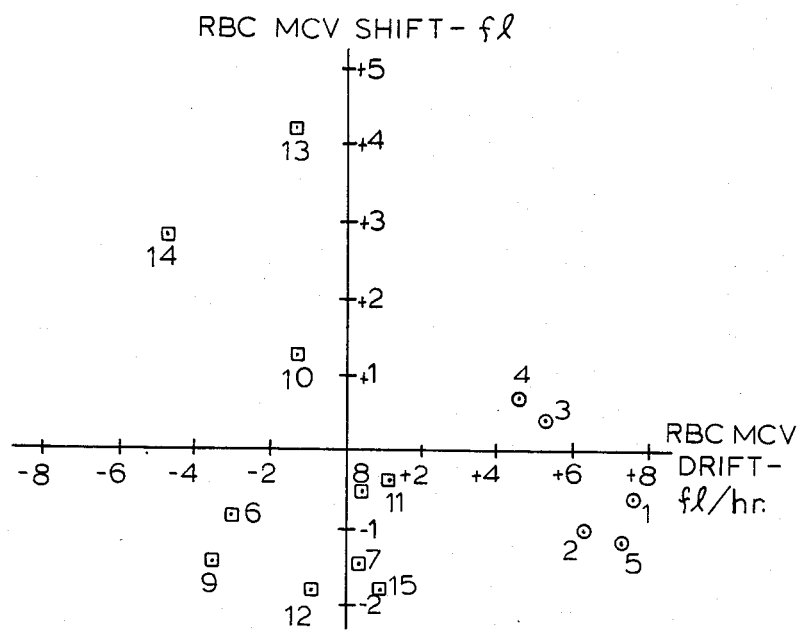

The single FIGURE is a graphic illustration of the position of several representative surfactants and preservatives on the opposite side of a red blood cell MCV shift line and a red blood cell drift line.

DETAILED DESCRIPTION OF THE INVENTION

In the single FIGURE, the effects of several representative surfactants and preservatives are shown. Shift is the change in RBC MCV observed on an electronic particle counter such as a Coulter Model Fn within 30 seconds after the dilution is made. The change is determined by a comparison of the observed MCV for a dilution in an isotonic diluent containing no preservative or surfactant and that observed for the same diluent containing the surfactant or preservative noted. Drift is the time rate of change of the RBC MCV observed over the first 30 minutes after the dilution is made. The drift rate is determined by the slope of a line fitted to the data obtained for the first 30 minutes by linear regression. The representative materials are as follows:

SURFACTANTS (1) PLURONIC F38—1 gm/l.
(2) PLURONIC F68—1 gm/l.
(3) PLURONIC F108—1 gm/l.
(4) TETRONIC T707—1 gm/ml.
(5) TETRONIC T908—1 gm/l.

PRESERVATIVES (6) 2 phenoxyethanol—2 ml/l.
(7) phenethyl alcohol—2 ml/l.
(8) benzyl alcohol—2 ml/l.
(9) sodium hypochlorite—0.53 ppm w/w
(10) sodium hypochlorite—5.00 ppm w/w
(11) mixed parabens—0.4 gm/l.
(12) chlorothymol—0.0083 gms/l.
(13) chlorhexidene diacetate—0.02 gms/l.
(14) benzethonium chloride—4.0 ppm w/w
(15) sodium hypochlorite 0.1 ppm w/w with Chloramine—T=2.0 ppm w/w As can be seen by selecting a surfactant with shift and drift values which are substantially equal in magnitude and opposite in direction to those of the preservatives, the effects of shift and drift of one may be neutralized by those of the other. In practice the effects are not usually strictly additive and some adjustment to the concentrations of surfactant and preservative may be necessary in order to bring the net effects on shift and drift to a minimum. For example, by choosing 2 phenoxyethanol and TETRONIC T707 the positive drift of T707 substantially balances the negative drift of 2 phenoxyethanol, as well as initial positive and negative shift effects of the diluent on a blood sample.

As purely illustrative of a procedure for obtaining the blood diluent of the invention, one may note the following example in which various combinations of diluents containing selected balanced preservative—surfactant combinations were made and compared with conventional diluents presently marketed as ISOTON II, a product of Coulter Diagnostics Inc., Hialeah, Fla. and described in U.S. Pat. No. 3,962,125 and DILUID 3, a product of J. T. Baker Chemicals, and described in U.S. Pat. No. 4,322,313.

EXAMPLE I

|  | Average of three readings | | | | | |
|---|---|---|---|---|---|---|
|  | RBC DRIFT | MCV SHIFT | MCV DRIFT |  | AVERAGE C.V. % | |
| DILUENT USED | %/hr. | fl | fl/hr. | RBC | MCV | Hct |
| DILUID 3 (Ref. MCV) | (−21.2/−20.3) | (83.0/91.3) | (2.7/1.9) | (.51/.59) | (.42/.73) | (1.04/1.03) |
| ISOTON II | −15.6/−16.5 | 2.0/1.0 | −1.6/−0.4 | .28/.32 | .64/.32 | .71/.42 |
| STOCK DILUENT (SD) | −22.1/−19.8 | 1.3/1.0 | 2.6/2.4 | .59/.39 | .41/.38 | .48/.60 |
| SD + 2 PE + T707 | 5.1/0.25 | 2.0/0.7 | −0.6/−2.5 | .36/.39 | .83/.59 | 1.11/.90 |
| SD + 2 PE + F108 | 1.8/1.1 | 2.3/1.0 | 2.1/−1.1 | .22/.44 | .27/.59 | .35/.59 |
| SD + T707 + Sodium Hypochlorite | 1.2/2.5 | 1.0/0.7 | 8.4/3.7 | .40/.40 | .27/.46 | .48/.80 |
| SD + F108 + Sodium Hypochlorite | 3.4/−0.5 | 1.3/0.7 | 6.8/7.6 | .48/.63 | .53/.45 | .44/.55 |

NOTE:
The first data are for a blood sample taken from one individual while the second data are for the second individual.

In this example, a stock diluent (SD) was prepared with the following formulation:

| STOCK DILUENT (SD) | |
|---|---|
| Component | Concentration |
| Sodium Chloride | 8.795 gms/liter |
| Potassium Chloride | 0.280 gms/liter |
| Potassium Phosphate, Monobasic | 0.260 gms/liter |
| Sodium Phosphate, Dibasic | 2.350 gms/liter |
| Disodium EDTA | 0.360 gms/liter |

The following four representative formulations were prepared:
1. 2 ml 2-phenoxyethanol+0.5 g TETRONIC 707+SD q.s. 1 liter
2. 2 ml 2-phenoxyethanol+0.5 g PLURONIC F108+SD q.s. 1 liter
3. Sodium hypochlorite final concentration=1.0 ppm+0.5 g TETRONIC T707+SD q.s. 1 liter
4. Sodium hypochlorite final concentration=1.0 ppm+0.5 g PLURONIC F108+SD q.s. 1 liter The following summary is made of the test results of blood samples taken from two different individuals selected from laboratory personnel.

| SUMMARY OF WHITE BLOOD CELL AND HEMOGLOBIN TEST RESULTS Average of Three (3) Readings | | | |
|---|---|---|---|
| DILUENT USED | WBC COUNT | C.V. % | A540 abs. |
| DILUID 3 | 5539/4757 | 1.35/0.60 | .1887/.1876 |
| ISOTON II | 5786/4985 | 0.84/1.11 | .1898/.1897 |
| STOCK DILUENT (SD) | 5562/4926 | 1.76/1.87 | .1843/.1809 |
| SD + 2 PE + T707 | 5967/5040 | 0.84/2.41 | .1964/.2006 |
| SD + 2 PE + F108 | 6018/5227 | 0.57/2.28 | .2038/.2013 |
| SD + Sodium hypochlorite + T707 | 5770/4960 | 1.40/1.18 | .1919/.1855 |
| SD + Sodium hypochlorite + F108 | 5914/5014 | 0.66/0.53 | .1915/.1864 |
| STOCK DILUENT (SD) | 5695/4879 | 0.45/1.48 | .1870/.1822 |

NOTE:
A540 absorbance is 1 cm light path on a Beckman DB-G, corrected for the absorbance of a diluent blank, and for the drift of absorbance with time.

The above data indicates that the balance preservative-surfactant combination of the invention increases WBC 3.2–5.0% compared to the stock diluent, 6.4–6.8% compared to DILUID 3, and 1.5–2.3% compared to ISOTON II.

The following data is a summary of Red Blood Cell Counts, and indicates RBC drift, Mean Corpuscular Volume (MCV) shift drift, and precision of RBC, MCV, and Hct for two blood samples.

As can be seen from the above data, MCV drift/shift is substantially equivalent to that of the stock diluent, thus indicating the balancing effect of the preservative-surfactant combination.

There is produced, in accordance with this invention, a blood diluent solution which has no significant effect on the mean corpuscular volume of red blood cells, which stabilizes the red blood cells so that they can be accurately measured, which diluent is an electrolyte capable of conducting current, and which has no significantly adverse effect on the white blood cells or platelets present in the sample. In addition, as a further feature of this invention, it should be noted that the diluent of this invention results in better dispersion of the cells in the diluent solution, and a reduction of gas bubbles attaching to fluid conduits at sensitive areas, such as the counting aperture of blood cell count instruments. The dispersion effect on the cells prevent the cells from adhering to the sample dilution vessel which would result in a loss of assayed concentration. These features result in more accurate and precise assays and also eliminate the need for rapid or timed RBC count assays of dilutions. It is anticipated that the use of surfactant and/or sodium hypochlorite will reduce the adherence of cells or cellular debris to critical portions of hematology analyzers such as filter screens, counting apertures, and hemoglobin flow cells and thus reduce the frequency of cleaning procedures.

The preparation of the diluent of the invention does not require special procedures, and the various components of the diluent may be added in any order and stirred to combine the various components together to form the solution. The combined blood sample-diluent is readily stabilized with no initial effect on the blood sample requiring an initial period of instability prior to any measurement. The diluent, prior to use, is isotonic with a neutral pH. Because of the proper balance between the preservative and surfactant components of the diluent, there is no significant swelling or shrinking of the cells as a result of the addition of the sample to the diluent.

While the compositions herein disclosed form preferred embodiments of this invention, this invention is not limited to the specific compositions and changes can be made therein without departing from the scope of the invention which is defined in the appended claims.

I claim:
1. A multi-purpose isotonic blood diluent composition for use in particle counting instrumentation, which diluent brings about rapid mean corpuscular volume stability, characterized by

(a) electrolytes selected from the group consisting of sodium chloride and potassium chloride, and mixtures thereof;
(b) pH buffers selected from the group consisting of monobasic phosphate and dibasic phosphate and mixtures thereof;
(c) ethylene diamine tetraacetic acid;
(d) a preservative; and
(e) an ethylene oxide-polypropylene condensation product present in an amount effective to balance the mean corpuscular volume of red blood cells added to the diluent in the presence of said preservative,
(f) whereby to bring about said rapid mean corpuscular volume stability.

2. The composition of claim 1, further characterized by
(a) said ethylene oxide-polypropylene condensation product is a non-ionic surfactant of polyoxyethylene-polyoxypropylene glycol containing 80% ethylene.

3. The composition of claim 1, further characterized by
(a) said sodium chloride is present within the range of between about 6 and 12 grams per liter;
(b) said potassium chloride is present within the range of between about 0 and 1 grams per liter;
(c) said monobasic phosphate is potassium dihydrogen phosphate present in the amount within the range of between about 0 and 1 grams per liter;
(d) said dibasic phosphate is disodium hydrogen phosphate present within the range of between about 0 and 5 grams per liter;
(e) said ethylene diamine tetracetic acid is present within the range of between about 0 and 1 grams per liter of disodium ethylene diamine tetraacetic acid;
(f) said preservative is 2 phenoxyethanol present within the range of between about 0.5 and 10 milliliters per liter; and
(g) said condensation product is present within the range of between about 0.001 and 10 grams per liter.

4. The composition of claim 3, further characterized by
(a) said condensation product is polyoxyethylene-polyoxypropylene glycol containing 80% ethylene oxide.

5. The composition of claim 3, further characterized by
(a) said 2 phenoxyethanol is present in the amount of 2.0 milliliters per liter; and
(b) said condensation product is present in the amount of 0.5 grams per liter.

6. The composition of claim 5, further characterized by
(a) said condensation product is polyoxyethylene-polyoxypropylene glycol containing 80% ethylene oxide.

7. The composition of claim 3, further characterized by
(a) said sodium chloride is present in the amount of 8.795 grams per liter;
(b) said potassium chloride is present in the amount of 0.28 grams per liter;
(c) said potassium dihydrogen phosphate is present in the amount of 0.26 grams per liter;
(d) said disodium hydrogen phosphate is present in the amount of 2.35 grams per liter;
(e) said ethylene diamine tetracetic acid is sodium ethylene diamine tetracetic acid present in the amount of 0.36 grams per liter;
(f) said 2-phenoxyethanol is present in the amount of 2.0 milliliters per liter; and
(g) said condensation product is polyoxyethylene-polyoxypropylene glycol containing 80% ethylene oxide and present in the amount of 0.5 grams per liter.

* * * * *